(12) United States Patent
Hunt et al.

(10) Patent No.: US 11,793,499 B2
(45) Date of Patent: Oct. 24, 2023

(54) REPLACEABLE BATTERY UNIT FOR A SURGICAL POWER TOOL

(71) Applicant: DEPUY IRELAND UNLIMITED COMPANY, Ringaskiddy (IE)

(72) Inventors: Christopher Hunt, Leeds (GB); Martin Reinberg, Leeds (GB); Duncan Young, Leeds (GB)

(73) Assignee: DePuy Ireland Unlimited Company, Ringaskiddy (IE)

( * ) Notice: Subject to any disclaimer, the term of this patent is extended or adjusted under 35 U.S.C. 154(b) by 766 days.

(21) Appl. No.: 16/960,352

(22) PCT Filed: Jan. 8, 2019

(86) PCT No.: PCT/EP2019/050313
§ 371 (c)(1),
(2) Date: Jul. 7, 2020

(87) PCT Pub. No.: WO2019/141536
PCT Pub. Date: Jul. 25, 2019

(65) Prior Publication Data
US 2021/0059649 A1    Mar. 4, 2021

(30) Foreign Application Priority Data
Jan. 16, 2018  (GB) ..................................... 1800696

(51) Int. Cl.
*A61B 17/00* (2006.01)
*A61B 17/16* (2006.01)
(52) U.S. Cl.
CPC .......... *A61B 17/00* (2013.01); *A61B 17/1666* (2013.01); *A61B 17/1628* (2013.01);
(Continued)

(58) Field of Classification Search
CPC ...... A61B 17/1628; A61B 2017/00734; A61B 17/00; A61B 17/1626; A61B 17/1659;
(Continued)

(56) References Cited

U.S. PATENT DOCUMENTS 4,871,033 A   10/1989 Odoni et al.
5,207,697 A   5/1993 Carusillo et al.
(Continued)

FOREIGN PATENT DOCUMENTS

CN   107530079 A   1/2018
EP   2205395 B1   1/2010
(Continued)

OTHER PUBLICATIONS

Corresponding Indian Application No. 202017028044—Examination Report dated Apr. 1, 2022.
(Continued)

*Primary Examiner* — Samuel S Hanna

(57) ABSTRACT

A replaceable battery unit for a surgical power tool and a method of operating a surgical power tool including the replaceable battery unit. The replaceable battery unit includes a housing containing one or more battery cells, a motion sensor unit, and a controller. The controller is operable to determine, from an output of the motion sensor unit, a sudden movement of the replaceable battery unit indicative of a kickback event of the surgical power tool. The controller is also operable, in response to the determination, to disconnect power from the replaceable battery unit to the surgical power tool.

15 Claims, 3 Drawing Sheets

(52) U.S. Cl.
CPC ............... *A61B 2017/00075* (2013.01); *A61B 2017/00734* (2013.01); *A61B 2560/0266* (2013.01); *A61B 2562/0219* (2013.01); *A61B 2562/0223* (2013.01)

(58) Field of Classification Search
CPC ........ A61B 17/1666; A61B 2560/0266; A61B 2562/0219; A61B 2562/0223; A61B 2017/00075
See application file for complete search history.

(56) References Cited

U.S. PATENT DOCUMENTS

| | | | |
|---|---|---|---|
| 5,984,020 | A | 11/1999 | Meyer et al. |
| 6,479,958 | B1 | 11/2002 | Thompson et al. |
| 10,160,049 | B2 | 12/2018 | Eshleman et al. |
| 2007/0084613 | A1 | 4/2007 | Zhang et al. |
| 2009/0248019 | A1 | 10/2009 | Falkenstein et al. |
| 2011/0114345 | A1 | 5/2011 | Schlesak et al. |
| 2013/0096539 | A1 | 4/2013 | Wood et al. |
| 2013/0105189 | A1 | 5/2013 | Murthy et al. |
| 2014/0166323 | A1 | 6/2014 | Cooper |
| 2014/0309666 | A1 | 10/2014 | Shelton, IV et al. |
| 2014/0321930 | A1 | 10/2014 | Dengler et al. |
| 2015/0182230 | A1* | 7/2015 | Belagali ............. A61B 17/1628 606/82 |
| 2017/0202607 | A1 | 7/2017 | Shelton, IV et al. |
| 2017/0258526 | A1 | 9/2017 | Lang |
| 2017/0361449 | A1 | 12/2017 | Goble |
| 2020/0029964 | A1 | 1/2020 | Overmyer et al. |

FOREIGN PATENT DOCUMENTS

| | | |
|---|---|---|
| EP | 2612733 A2 | 1/2010 |
| EP | 2792313 A2 | 10/2014 |
| JP | 2013-516335 | 7/2014 |
| WO | 2009032314 A1 | 3/2009 |
| WO | 2013177423 A2 | 11/2013 |

OTHER PUBLICATIONS

PCT/EP2019/050313—International Search Report dated Apr. 12, 2019.
AU2012265600A1_English Abstract.

* cited by examiner

REPLACEABLE BATTERY UNIT FOR A SURGICAL POWER TOOL

This application is a National Stage Application filed Under 35 U.S.C. § 371 of International Application No. PCT/EP2019/050313 filed Jan. 8, 2019, which claims priority to GB priority application 1800696.5 filed Jan. 16, 2018, which are both hereby incorporated by reference in their entireties.

FIELD OF THE INVENTION

This invention relates to a replaceable battery unit for a surgical power tool. This invention also relates to a surgical kit including the replaceable battery unit or a surgical power tool including the replaceable battery unit. This invention further relates to a method of operating a surgical power tool including the replaceable battery unit.

BACKGROUND OF THE INVENTION

Surgeons using surgical power tools can be injured from wrist strain caused by kickback during procedures such as acetabular reaming. It is known to include torque limiters within the power tool, but these can hinder the surgical work flow and so tend to be overridden by the user.

US 2014/0166323 A1 describes an apparatus and methods for protecting an operator from sudden, unexpected or dangerous movement of powered hand held tools and the like. A set of parameters for safe operation of the tool are provided, which parameters may be adjusted or selected based on the manner in which the tool is being operated. The power tool is fitted with sensors including an accelerometer, operating to sense acceleration of the tool in a plurality of axes during operation. The output of the accelerometer is coupled to a computing circuit which determines if the acceleration of the tool is within the safe operation parameters. When acceleration of the tool exceeds one or more of the safe operating parameters, power to the tool motor is limited or otherwise adjusted in order to prevent or reduce the movement of the tool thereby protecting the operator.

U.S. Pat. No. 5,984,020 A describes a tool including an inertia responsive element. The power tool comprises a housing, a motor supported by the housing and adapted to be connected to a power source, an output element supported by the housing and selectively coupled to the motor, the motor imparting motion to the output element, and an inertia responsive element for disconnecting the output element from the power source if movement of the housing is greater than a predetermined threshold. The power tool may be a hand held power tool having a handle, and the inertia responsive element disconnects the output element from the power source should the handle move at a rate greater than a predetermined rate. The power tool may be a stationary power tool, such as a drill press. The housing of the stationary power tool includes a base for supporting the stationary power tool on the workpiece. The base is selectively connectable to the workpiece so that, when the base is connected to the workpiece, the housing is substantially stationary relative to the workpiece. The inertia responsive element disconnects the output element from the power source when the housing moves relative to the workpiece at a rate greater than a predetermined rate.

US 2011/0114345 A1 describes a handheld power tool device, having at least one safety mechanism, which intervenes in an uncontrolled blocking situation, and which has a sensor unit. The sensor unit is provided for directly detecting at least one orientation parameter of a handheld power tool.

US 2007/0084613 A1 describes a control system that is provided for use in a power tool. The control system includes: a rotational rate sensor having a resonating mass and a controller electrically connected to the rotational rate sensor. The rotational rate sensor detects lateral displacement of the resonating mass and generates a signal indicative of the detected lateral displacement, such that the lateral displacement is directly proportional to a rotational speed at which the power tool rotates about an axis of the rotary shaft. Based on the generated signal, the controller initiates a protective operation to avoid further undesirable rotation of the power tool. The controller may opt to reduce the torque applied to shaft to a non-zero value that enables the operator to regain control of the tool.

EP 2 205 395 B1 describes a power tool including a housing and a motor assembly in the housing. The motor assembly can include an output member and a motor for translating the output member. A kickback sensor can sample successive periods of current through the motor and produce an output in response thereto. An anti-kickback control device can remove energy from the output member in response to the output of the kickback sensor. A switch can have a first setting and a second setting. The first setting can correspond to a first operating condition of the anti-kickback control device. The second setting can correspond to a second operating condition of the anti-kickback control device.

US 2014/0321930 A1 describes a hand tool operating unit that includes at least one operating member, and an electronic operating unit that has a position sensor configured to ascertain a position of the operating member. The hand tool operating unit additionally includes at least one further sensor that is configured to ascertain at least one characteristic variable.

U.S. Pat. No. 6,479,958 B1 describes that a rapid increase in motor current (di/dt above a predetermined threshold) causes a motor control system to enter pulse mode operation in which the motor current is pulsed on and off rapidly to dislodge the workpiece obstruction or binding condition that would otherwise lead to a motor stall. When the workpiece obstruction or binding has been cleared, the motor resumes normal operation.

US 2013/0105189 A1 describes a power tool that includes a housing, a motor disposed in the housing, a transmission disposed in the housing and coupled to the motor, an output end effector coupled to the transmission, a control circuit for controlling power delivery from a power source to the motor, and a force sensing electronic clutch including a force sensor coupled to a substantially stationary element of the transmission. The force sensor senses a reaction torque transmitted from the end effector to at least a portion of the transmission. The sensor is configured to generate a first electronic signal corresponding to an amount of the reaction torque. The control circuit compares the first electronic signal with a second electronic signal corresponding to a desired threshold torque value, and initiates a protective operation when a value of the first electronic signal indicates that the reaction torque has exceeded the desired threshold torque value.

U.S. Pat. No. 4,871,033 A describes that, in a motor-driven hand tool, such as a drill, an inert mass is rotatably supported in a housing and is connected to the housing by a spring encircling a driven shaft mounted in the housing. The driven shaft is arranged to rotate a drill bit secured to the shaft. If the driven shaft is prevented from rotating and the housing rotates relative to the shaft, the spring tightens about and grips the driven shaft exerting a braking torque on it. The braking torque reduces the reaction torque required of the tool operator and affords a more rapid release of an overload clutch acting on the driven shaft. The overload clutch is formed by a collar, a gear wheel, a cup spring, and an adjustable ring nut, all located on the driven shaft.

EP 2 612 733 A2 describes a tool that has an electric motor for rotational driving of a to-be-driven element i.e. drill bit. A braking block is used for braking the motor, and a detection unit i.e. gyroscopic sensor, detects rotational driving of the tool for controlling the braking block of the motor. The motor includes a contactor i.e. electromechanical contactor, arranged to isolate the motor from electrical supply and to transform the motor into current generator whose current is re-injected into reversed polarity of the motor.

US 2013/096539 A1 describes a handheld device that includes an electronic instrument and a capacitive power supply for storing and delivering power to the electronic instrument. The capacitive power supply includes at least one capacitor, and an electronic circuit operable to boost a voltage from the capacitor to a higher voltage for use by the electronic instrument. The capacitive power supply can be rapidly recharged. Some configurations include an accelerometer which permits the handheld device to detect movement and perform various operations responsive to detected movement. A dual charging station is also disclosed.

US 2017/202607 A1 describes a surgical instrument that comprises a controller configured to control application of RF or ultrasonic energy at a low level when displacement or intensity of a button is above a first threshold but below a second threshold higher than the first threshold, and control application of RF or ultrasonic energy at a high level when the displacement or intensity exceeds the second threshold. A surgical instrument is also described, that comprises a first sensor configured to measure a tissue characteristic at a first location, a second sensor configured to measure the tissue characteristic at a second location, and a controller configured to, based at least in part on the measured tissue characteristic at the first location and the second location, control application of RF or ultrasonic energy.

SUMMARY OF THE INVENTION

Aspects of the invention are set out in the accompanying independent and dependent claims. Combinations of features from the dependent claims may be combined with features of the independent claims as appropriate and not merely as explicitly set out in the claims.

According to an aspect of the invention, there is provided a replaceable battery unit for a surgical power tool, the replaceable battery unit comprising a housing containing:
  one or more battery cells;
  a motion sensor unit; and
  a controller operable to:
    determine, from an output of the motion sensor unit, a sudden movement of the replaceable battery unit indicative of a kickback event of the surgical power tool; and
    in response to the determination, disconnect power from the replaceable battery unit to the surgical power tool.

The inclusion of a motion sensor unit and the controller in a replaceable battery unit for a surgical power tool may allow kickbacks to be detected in a manner that can allow existing surgical power tools retrospectively to be provided with protection against kickback events. Another benefit of including the motion sensor unit and the controller in a replaceable battery unit for a surgical power tool is that any electronics forming these features do not need to be sterilized. The replaceable battery unit containing these features may simply be loaded into the surgical power tool before the surgical procedure using aseptic transfer.

A kickback in a surgical power tool may result in a sudden movement of the power tool, but may also lead to a change in the current flow to a motor of the surgical tool. For instance, this change in current flow may be associated with a change in torque applied by the motor as an instrument such as a rotational reamer attached to the power tool digs in and catches on a bone surface. The replaceable battery unit may further include a current sensor for sensing a flow of current to a motor of the surgical power tool. The controller may be further operable to determine, from an output of the motion sensor unit and from an output of the current sensor, whether a sudden movement of the replaceable battery unit is indicative of a kickback event of the surgical power tool. In this way, the controller may discriminate between an actual kickback and a false positive associated with movements of the power tool that are not the result of a kickback. For instance, the controller may be operable to determine, from an increase in current sensed by the current sensor, that a contemporaneous, sudden movement of the replaceable battery unit sensed by the motion sensor unit is indicative of a kickback event of the surgical power tool. The increase in current may be associated with the above mentioned change in torque applied by the motor.

The motion sensor unit comprises at least one of:
  a gyroscope;
  an accelerometer; or
  a magnetometer.

The motion sensor unit may be an inertial measurement unit (IMU).

In one embodiment, the replaceable battery unit may include a brake for short circuiting windings of a motor of the surgical power tool in response to said determination of a sudden movement of the replaceable battery unit indicative of a kickback event of the surgical power tool. This can allow for swift braking of the motor.

In one embodiment, the sudden movement of the replaceable battery unit may be a rotational movement. The rotational movement may, for instance, be associated with an acetabular reamer catching with an inner surface of an acetabulum, causing the surgical power tool to kickback by rotating suddenly around a rotational axis of the reamer.

In one embodiment, the sudden movement of the replaceable battery unit may be a linear movement.

The one or more battery cells may be rechargeable.

According to another aspect of the invention, there is provided a surgical power tool including a replaceable battery unit of the kind described above.

The surgical power tool may include a body portion. The surgical power tool may also include a handle extending outwardly from the body portion. The replaceable battery unit may be attached to, or received at least partially inside, the handle. By locating the battery having the motion sensor unit on or in the handle, the motion sensor unit can be situated close to the surgeon's hand, for improved detection of sudden movements that may injure the surgeon.

The replaceable battery unit may be attached to, or received at least partially inside, an end of the handle distal the body portion. At a location distal the body portion, the replaceable battery unit including the motion sensor unit may be best placed for detecting sudden movements, particularly those associated with sudden rotations of the body portion.

The surgical power tool may be a rotational power tool, for example a drill or device for applying torque to a rotational reamer.

According to a further aspect of the invention, there is provided a surgical kit. The surgical kit may include one or more replaceable battery units of the kind described above. The surgical kit may also include one or more surgical power tools configured to receive the one or more replaceable battery units.

According to another aspect of the invention, there is provided a surgical kit including at least one surgical power tool of the kind described above.

According to a further aspect of the invention, there is provided a method comprising:

operating a surgical power tool of the kind described above; and during the operation of the surgical power tool, the controller:

determining, from an output of the motion sensor unit, a sudden movement of the replaceable battery unit indicative of a kickback event of the surgical power tool; and in response to the determination, disconnecting power from the replaceable battery unit to the surgical power tool.

BRIEF DESCRIPTION OF THE DRAWINGS

Embodiments of the present invention will be described hereinafter, by way of example only, with reference to the accompanying drawings in which like reference signs relate to like elements and in which.

DETAILED DESCRIPTION

Embodiments of the present invention are described in the following with reference to the accompanying drawings.

Figure 1:
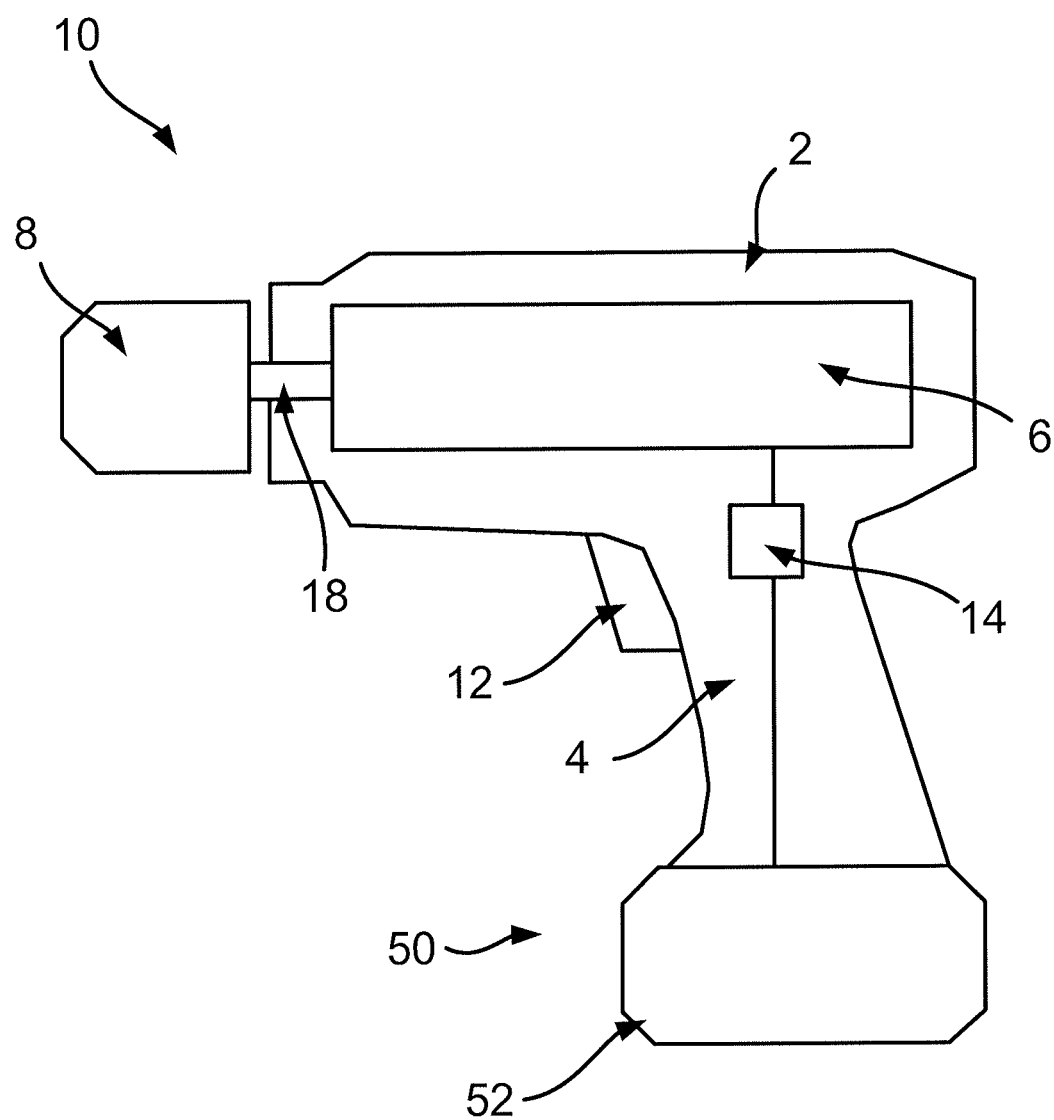
FIG. 1 shows a surgical power tool including a replaceable battery unit according to an embodiment of this invention.

FIG. 1 shows a surgical power tool 10 including a replaceable battery unit 50 according to an embodiment of this invention. The surgical power tool 10 includes a body portion 2. The surgical power tool 10 also includes a handle 4, with which a surgeon may hold the surgical power tool 10. The handle 4 may extend outwardly from the body portion 2. The surgical power tool 10 may also include a chuck 8. The chuck 8 may include attachment features for attaching surgical instruments such as reamers (e.g. rotational reamers for use in reaming the acetabulum of a patient or reamers for reaming a femoral head for a resurfacing implant), surgical drill bits, pins, threaded pins, burrs, and such like, to the surgical power tool 10.

The surgical power tool 10 also includes a motor 6, which is powered by the replaceable battery unit 50 to be described below. The motor 6 may be operable to apply torque to a shaft 18, which in turn may be connected to the chuck 8. The surgical power tool 10 may further include a motor controller 14. The motor controller 14 may control the operation of the motor 6. For instance, the to the surgical power tool 10 may include a button 12 for operating the surgical power tool 10. The motor controller 14 may be operable to switch on the motor 6 when it detects that the button 12 has been pressed. The button 12 may be located on the handle 4 to allow it to be conveniently pressed by a finger of the surgeon's hand that grips the handle 4.

The body portion 2 and handle 4 of the surgical power tool 10 may comprise an outer housing that contains and protects the motor 6, shaft 18 and motor controller 14. The outer housing may comprise, for example, a plastics material.

FIG. 1 also shows a replaceable battery unit 50. The replaceable battery unit 50 may be attached to, or received at least partially inside the housing of the surgical power tool 10.

In this embodiment, the replaceable battery unit 50 is attached to an end of the handle 4 distal the body portion 2. It is also envisaged that the replaceable battery unit 50 may be received at least partially inside (e.g. the distal end of) the handle 4. It is further envisaged that the replaceable battery unit 50 may be provided in a compartment located inside the surgical power tool 10 (e.g. in the handle 4). The compartment my include a hatch for accessing and replacing the replaceable battery unit 50.

The surgical power tool 10 and the replaceable battery unit 50 may be provided with corresponding connection features for attaching the replaceable battery unit 50 to the surgical power tool 10. The corresponding connection features may include features for completing an electrical connection between the surgical power tool 10 and the replaceable battery unit 50, so that the replaceable battery unit 50 can supply electrical power to the motor 6. The corresponding connection features may also include a release mechanism, such as a catch operated by a button, to allow the replaceable battery unit 50 to be detached from the surgical power tool 10.

In this example, the replaceable battery unit 50 has a housing 52, which may contain and provide protection for the features of the replaceable battery unit 50 to be described below. As noted previously, a benefit of including features such as a motion sensor unit and a controller of the kind described herein in a replaceable battery unit 50 is that any electronics forming these features do not need to be sterilized (e.g. owing to the protection for these features provided by the housing 52). The replaceable battery unit 50 containing these features may simply be loaded into the surgical power tool 10 before the surgical procedure using aseptic transfer. The housing 52 may, for instance, comprise a plastics material.

Figure 2:
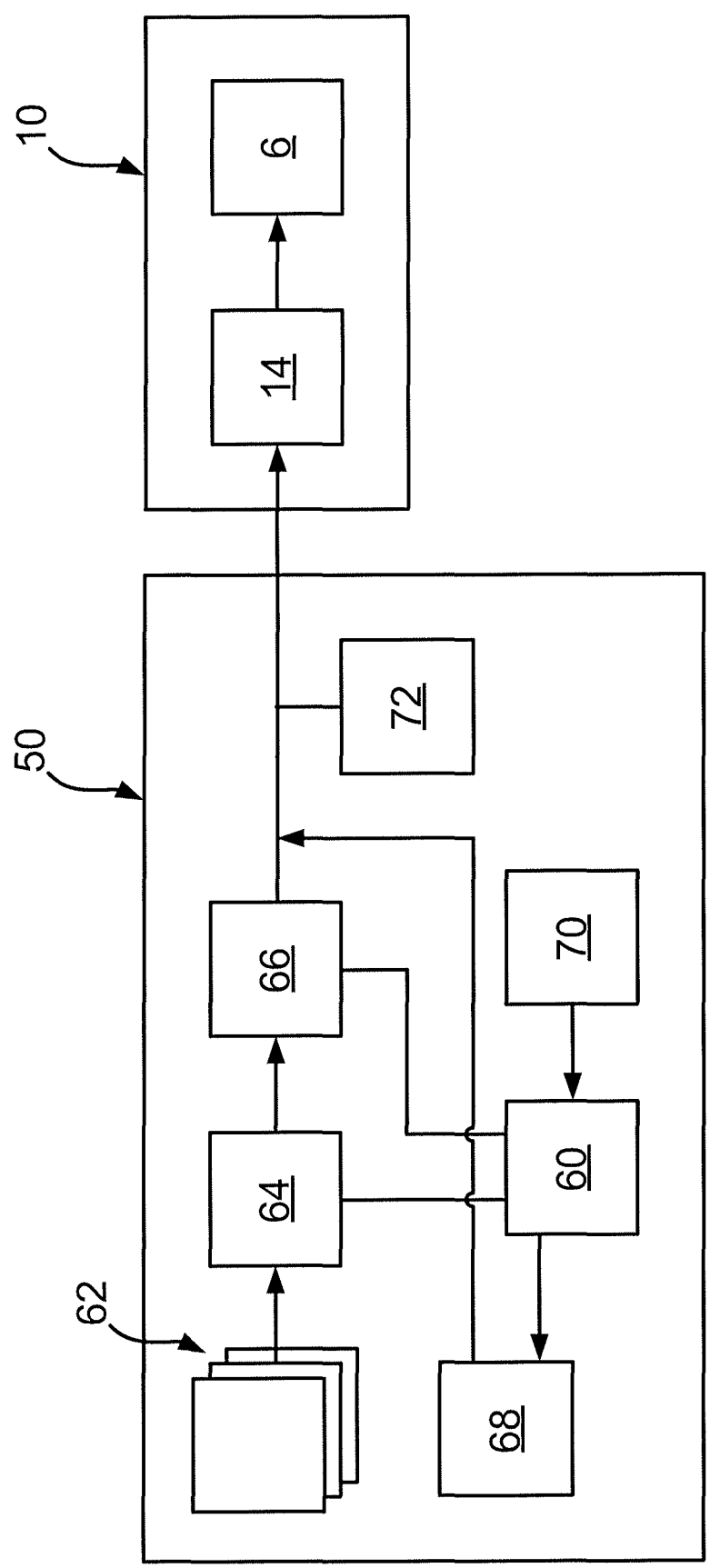
FIG. 2 shows a schematic of the functional components of a surgical power tool and a replaceable battery unit according to an embodiment of this invention.

FIG. 2 shows a schematic of the functional components of a surgical power tool 10 and a replaceable battery unit 50 according to an embodiment of this invention.

As noted above, the surgical power tool 10 may include a motor 6. The motor 6 is connected to a motor controller 14. The features of the replaceable battery unit 50 in this embodiment will now be described.

The replaceable battery unit 50 includes one or more battery cells 62. The battery cells 62 may be rechargeable. The battery cells 6 may be of any suitable kind, e.g. nickel-cadmium (NiCd), nickel-metal hydride (NiMH), lithium-ion (Li-ion), lithium-ion polymer (Li-ion polymer) or lithium-iron-phosphate (LiFePO4/LFP).

The replaceable battery unit 50 also includes a motion sensor unit 70. The motion sensor unit 70 may include one or more of the following: a gyroscope; an accelerometer; or a magnetometer. The gyroscope may be a 1D, 2D or 3D gyroscope. The accelerometer may be a 1D, 2D or 3D accelerometer. The magnetometer may be a 1D, 2D or 3D magnetometer. It is envisaged that the motion sensor unit 70 may include combinations of these sensor types. It is envisaged that the motion sensor unit 70 may be an inertial measurement unit (IMU).

The motion sensor unit 70 may be used to detect movements of the replaceable battery unit 50. A sudden movement of the replaceable battery unit 50 may be indicative of a kickback event of the surgical power tool 10. The motion sensor unit 70 may be configured (e.g. oriented within the replaceable battery unit 50 so as to detect movements of the replaceable battery unit 50 in directions, or (in the case of rotational movements) around axes that would normally be associated with a kickback event of the surgical power tool 10.

Figure 3:
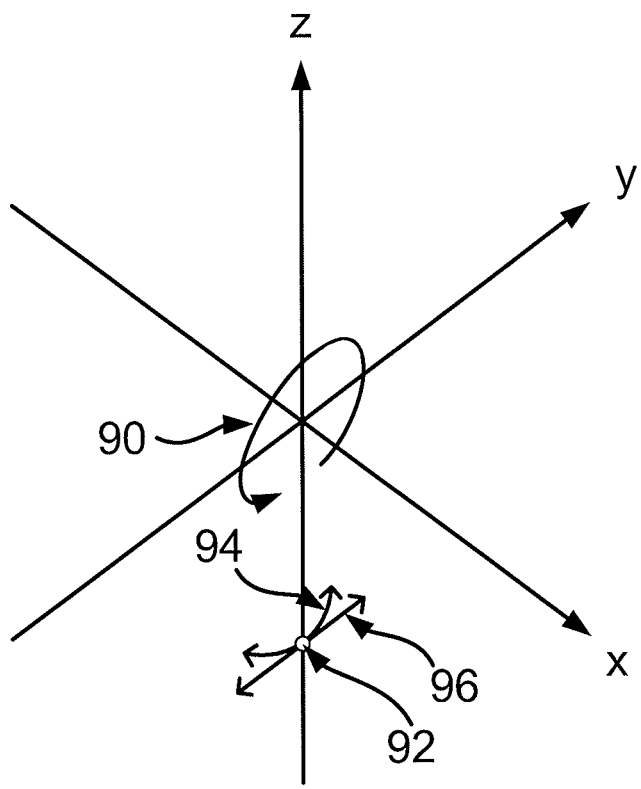
FIG. 3 schematically illustrates movements of a surgical power tool that may be detected by a motion sensor unit of a replaceable battery unit according to an embodiment of this invention.

FIG. 3 schematically illustrates movements of a surgical power tool 10 that may be detected by a motion sensor unit 70 of a replaceable battery unit 50 according to an embodiment of this invention. In FIG. 3, it is assumed that the surgical power tool is located at the centre of the Cartesian coordinates, with the rotational axis of the shaft 18 oriented along the x-axis. It is also assumed that the motion sensor unit 70 of the replaceable battery unit 50 is located at position 92. For instance, the replaceable battery unit 50 may be attached to, or received at least partially inside the handle 4 as described above, with the handle extending along the negative z direction.

During a kickback event, a surgical instrument such as a reamer or drill bit attached to the chuck 8 may dig in and catch on a bone surface of the patient. This can cause the surgical power tool 10 to begin to rotate around the rotational axis of the shaft 18 (the x-axis in this example), as illustrated by the arrow in FIG. 3 labeled 90. At position 92 this may cause the motion sensor unit 70 to begin to move in an arc curving upwards towards the x-y plane, as indicated by the arrow labeled 94 in FIG. 3. The direction of movement of the motion sensor unit 70 (i.e. towards the positive y direction or the negative y direction) depends upon the direction of rotation of the shaft 18 prior to the kickback event.

For small movements, or for locations 92 that are sufficiently far away from the axis of rotation of the shaft 18 (the x-axis in this example), the movement of the motion sensor unit 70 may be approximated to be linear (as indicated by the arrow labeled 96 in FIG. 3). The motion sensor unit 70 may include sensor devices for detection rotational and/or linear movements.

For efficient detection of movements by the motion sensor unit 70, features thereof such as a gyroscope, accelerometer and/or magnetometer may be oriented within the replaceable battery unit 50 such that their natural axis/axes for detection of movement are aligned consistent with the anticipated movement of replaceable battery unit 50 in a kickback event. For instance, in the case of a 1D/2D/3D gyroscope, an axis of the gyroscope may be aligned parallel to an axis of rotation of the surgical power tool 10 (e.g. the axis of rotation of the shaft 18 as described previously). In the example of FIG. 3, an axis of a 1D/2D/3D gyroscope may be aligned parallel with the x-axis.

Returning to FIG. 2, the replaceable battery unit 50 further includes a controller 60. The controller 60 is connected to the motion sensor unit 70. The controller 60 may be operable to monitor an output of the motion sensor unit 70 to determine therefrom the detection of a sudden movement of the replaceable battery unit 50. In order to distinguish normal motions of the replaceable battery unit 50 from sudden motions that may be associated with a kickback event, the controller 60 may be able to apply certain algorithms to the data outputted by the motion sensor unit 70. These algorithms may, for instance, involve the comparison of the output data with certain threshold values. In the event that these threshold values are reached or exceeded, the controller 60 may conclude that a kickback event is occurring.

In embodiments in which the motion sensor unit 70 includes more than one kind of sensing device (e.g. a gyroscope plus an accelerometer, a gyroscope plus a magnetometer, an accelerometer plus a magnetometer, or a gyroscope plus an accelerometer plus a magnetometer), the controller 60 may be operable to compare data received from each. In this way, false positives may be reduced (e.g. a kickback event may only be determined if the data from all, or a majority, of the sensing devices of the motion sensor unit 70 are indicative of a sudden movement). As will be described below, the controller 60 may also be operable to consider other factors, such as the current flow to the motor 6, when determining whether a kickback event is taking place.

The controller 60 is operable, upon determining that an output of the motion sensor unit 70 is consistent with a sudden movement of the replaceable battery unit 50 that is indicative of a kickback event of the surgical power tool 10, to disconnect power from the replaceable battery unit to the surgical power tool 10. The inclusion of a motion sensor unit 70 and the controller 60 in a replaceable battery unit 50 for a surgical power tool may allow kickbacks to be detected in a manner that can allow existing surgical power tools retrospectively to be provided with protection against kickback events. Moreover, in embodiments in which the replaceable battery unit 50 is attached to, or at least partially received within, an extremity of the surgical power tool 10, the motion sensor unit 70 may be positioned away from the rotational axis of the shaft 18. This can improve the sensitivity of the motion sensor unit 70 for detecting kickback events causing with sudden movements of the surgical power tool 10 around the rotational axis of the shaft 18. For instance, as described in relation to FIG. 1, the replaceable battery unit 50 may be attached to, or at least partially received within, an end of the handle 4 distal the body portion 2 that contains the motor 6 and the shaft 18. In this position, the motion sensor unit 70 may be optimally placed for detecting sudden movements of the surgical power tool 10 around the rotational axis of the shaft 18, while also allowing for convenient installation of the replaceable battery unit 50 in or on the handle 4. It is also noted that by locating the replaceable battery unit 50 having the motion sensor unit 70 on or in the handle 4, the motion sensor unit 70 can be situated close to the surgeon's hand, for improved detection of sudden movements that may injure the surgeon.

The replaceable battery unit 50 may also include a power switch 66 such as a transistor. The controller 60 may be connected to a control terminal of the power switch 66. The controller 60 may be operable to use the power switch 66 to connect and (e.g. during a kickback event as described herein) disconnect power from the replaceable battery unit 50 to the surgical power tool 10.

The replaceable battery unit 50 may also include a power supply unit 68. The power supply unit 68 may draw power from the one or more battery cells 62 for powering the other components of the replaceable battery unit 50, such as the controller 60 and the motion sensor unit 70. The power supply unit 68 may comprise a voltage converter. The power supply unit 68 may have a low power standby mode (>1 uA). In one embodiment, the power supply unit 68 may have a wake-up function that detects the attachment/insertion of the replaceable battery unit 50 to/in a surgical power tool 10 and powers up the controller 60 and optionally also further components such as the motion sensor unit 70. In one embodiment, the controller 60 may be operable to power down the replaceable battery unit 50 (e.g. where removal of the replaceable battery unit 50 from the surgical power tool 10 is detected, or when a time-out condition is met (i.e. in which it is determined that the surgical power tool 10 has not been used for some time)).

As described herein, a kickback in the surgical power tool 10 may result in a sudden movement of the surgical power tool 10. However, a kickback may also result in changes in the current flow to the motor 6. This may be associated with a change in torque applied by the motor 6 as an instrument such as a rotational reamer attached to the surgical power tool 10 digs in and catches on a bone surface. In accordance with an embodiment of this invention, these changes in current may be detected and used as further indicators that a kickback event is taking place.

As shown in FIG. 2, the replaceable battery unit 50 may further include a current sensor 64. The controller 60 may be connected to the current sensor 64, to receive an output of the current sensor 64 indicative of the flow of current to the motor 6 of the surgical power tool 10. The controller 60 may be operable to determine, from the output of the motion sensor unit 70 and from the output of the current sensor 64, whether a sudden movement of the replaceable battery unit 50 is indicative of a kickback event of the surgical power tool 10.

In this way, the controller may discriminate between an actual kickback and a false positive associated with movements of the surgical power tool 10 that are not the result of a kickback. For instance, the controller 60 may be operable to determine that a sudden movement of the replaceable battery unit 50 is not associated with a kickback event if there is no contemporaneous change in the output of the current sensor 64.

In one embodiment, an increase in current to the motor 6 sensed by the current sensor 64, contemporaneous with a sudden movement of the replaceable battery unit 50 sensed by the motion sensor unit 70 may be interpreted by the controller 60 as being indicative of a genuine kickback event. The increase in current itself may be associated with an increase in torque applied by the motor 6 as the surgical instrument digs in and catches on a bone surface as described above.

In one embodiment, the motion sensor unit 70 may include a 1D gyroscope. The gyroscope may be oriented to detect changes in angular velocity about the axis of rotation of the surgical power tool 10 (e.g. the axis of rotation of the shaft 18 as described previously). A motion sensor unit 70 of this kind may also be used in conjunction with a current sensor 64 of the kind described above, to allow the controller 60 to reduce false positives by determining whether a sudden movement of the surgical power tool 10 is contemporaneous with an increase in current to the motor 6 associated with an increase in torque applied by the motor 6.

As described herein, the motion sensor unit 70 may include features operable to determine sudden movements of the replaceable battery unit 50 having more than one directional component. For instance, the motion sensor unit 70 may include a 2D/3D gyroscope, 2D/3D accelerometer and/or 2D/3D magnetometer as described in more detail below. This may allow the motion sensor unit 70 to reduce the number of false positives detected by the replaceable battery unit 50 compared to embodiments using, e.g. a 1D gyroscope, 1D accelerometer or 1D magnetometer. For instance, using a 2D/3D gyroscope, 2D/3D accelerometer and/or 2D/3D magnetometer may allow corrections to be made for misalignments between the motion sensor unit 70 and the axis of rotation of the surgical power tool 10. The use of features operable to determine sudden movements of the replaceable battery unit 50 having more than one directional component as described here may also allow for more accurate characterization of a kick back event if it is known, for example, that a kick back generally manifests itself as a movement relative to more than one axis. It is envisaged that the functionality described here (i.e. determination of sudden movements of the replaceable battery unit 50 having more than one directional component) may also be achieved by using combinations of more than one sensor (e.g. a 1D gyroscope combined with a 1D/2D/3D accelerometer).

It is envisaged that a calibration step may performed prior to the use of the surgical power tool 10, by which the readings taken in a coordinate system of the motion sensor unit 70 could be converted/resolved into a coordinate system based on the actual axis of rotation of the surgical power tool 10. This can allow the above mentioned misalignment of the motion sensor unit 70 relative to the axis of rotation of the surgical power tool 10 to be corrected for.

In one embodiment, the motion sensor unit 70 may include a 3D gyroscope. The 3D gyroscope may to detect changes in angular velocity of the surgical power tool 10. These changes may be changes about the normal axis of rotation of the surgical power tool 10 (e.g. the axis of rotation of the shaft 18 as described previously), but may also include changes in angular velocity about other axes. As mentioned above, this may allow the motion sensor unit 70 to reduce the number of false positives detected by the replaceable battery unit 50 and/or allow for more accurate characterization of a kickback event compared to embodiments using a 1D gyroscope.

In a further embodiment, the motion sensor unit 70 may include an accelerometer. The accelerometer may be a 1D, 2D or 3D accelerometer. In such embodiments, the controller 60 may be operable to determine a sudden movement of the replaceable battery unit 50 from the acceleration signal provided by the accelerometer and/or its derivative. In one embodiment, the controller 60 may be operable to apply an algorithm that compares the acceleration signal and/or its derivative to the acceleration profile associated with a typical kickback event. It is also envisaged that instead of 1D, 2D or 3D accelerometer, a 1D, 2D or 3D magnetometer may be used. A motion sensor unit 70 including a 1D, 2D or 3D accelerometer or a 1D, 2D or 3D magnetometer may also be used in conjunction with a current sensor 64 of the kind described above, to allow the controller 60 to reduce false positives by determining whether a sudden movement of the surgical power tool 10 is contemporaneous with an increase in current to the motor 6 associated with an increase in torque applied by the motor 6.

In another embodiment, the motion sensor unit 70 may include a 3D accelerometer, a 3D magnetometer, a 3D gyroscope and a current sensor 64. It is envisaged that by basing the determination a kickback event on the outputs of each 3D sensor device of the motion sensor unit 70, and combining it with detection of the current flowing to the motor 6, robust detection of kickbacks may be achieved with a low number of false positives.

The replaceable battery unit 50 may also include a brake 72 for short circuiting windings of the motor 6 of the surgical power tool 10 in response to a determination that sudden movement of the replaceable battery unit 50 is indicative of a kickback event of the surgical power tool 10. This can allow for swift braking of the motor 6.

In one embodiment, a surgical kit may be provided that includes one or more replaceable battery units 50 of the kind described herein. The surgical kit may also include one or more surgical power tools 10 configured to receive the one or more replaceable battery units 50. In one embodiment, a surgical kit may be provided that includes at least one surgical power tool 10 of the kind described herein, each surgical power tool 10 having a replaceable battery unit 50 installed.

Figure 4:
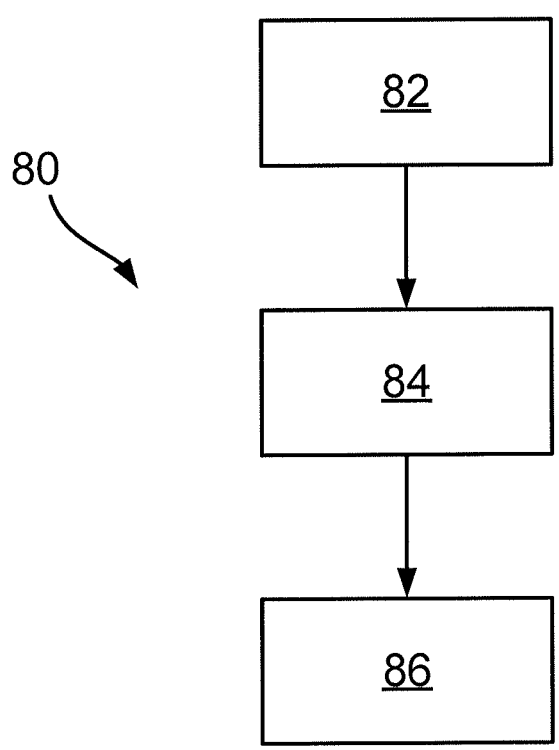
FIG. 4 shows a method according to an embodiment of this invention.

FIG. 4 shows a number of steps in a method 80 according to an embodiment of this invention.

In a first step 82, the method 80 includes operating a surgical power tool 10 of the kind described above. Step 82 may form a part of various different kinds of surgical procedures. In one example, step 82 involves using a surgical drill bit attached to the (e.g. chuck 8 of the) surgical power tool 10 to drill into bone. In another example, step 82 involves using a rotational reamer attached to (e.g. the chuck 8 of) the surgical power tool 10 to ream an inner surface of an acetabulum during the hip replacement procedure. Step 82 may generally involve the surgeon holding (e.g. the handle 4 of) the surgical power tool 10 while the motor 6 applies torque to the surgical instrument that is attached to the surgical power tool 10.

Step 84 is carried out during the operation of the surgical power tool 10. Step 84 includes the controller 60 determining, from an output of the motion sensor unit 70, that a sudden movement of the replaceable battery unit 50 is indicative of a kickback event of the surgical power tool. Step 84 may involve applying algorithms of the kind noted above to an output of the motion sensor unit 70. Step 84 may also involve monitoring an output of the current sensor 64 to check whether a sudden movement of the replaceable battery unit 50 indicated by the motion sensor unit 70 is contemporaneous with a change in current to the motor 6, as described above.

In step 86, in response to the determination of a kickback event, the controller disconnects power from the replaceable battery unit 50 to the surgical power tool 10. This may involve the controller 60 applying a control signal to the power switch 66 to disconnect the power. Step 86 may also involve operating the brake 72, for swift braking of the motor 6.

Accordingly, there has been described a replaceable battery unit for a surgical power tool and a method of operating a surgical power tool including the replaceable battery unit. The replaceable battery unit includes a housing containing one or more battery cells, a motion sensor unit, and a controller. The controller is operable to determine, from an output of the motion sensor unit, a sudden movement of the replaceable battery unit indicative of a kickback event of the surgical power tool. The controller is also operable, in response to the determination, to disconnect power from the replaceable battery unit to the surgical power tool.

Although particular embodiments of the invention have been described, it will be appreciated that many modifications/additions and/or substitutions may be made within the scope of the claimed invention.

The invention claimed is:

1. A replaceable battery unit for a surgical power tool, the replaceable battery unit comprising a housing containing:
   one or more battery cells;
   a motion sensor unit; and
   a controller operable to:
      determine, from an output of the motion sensor unit, a sudden movement of the replaceable battery unit indicative of a kickback event of the surgical power tool; and
      in response to said determination, disconnect power from the replaceable battery unit to the surgical power tool.

2. The replaceable battery unit of claim 1, wherein the replaceable battery unit further includes a current sensor for sensing a flow of current to a motor of the surgical power tool, and wherein the controller is further operable to determine, from an output of the motion sensor unit and from an output of the current sensor, whether a sudden movement of the replaceable battery unit is indicative of a kickback event of the surgical power tool.

3. The replaceable battery unit of claim 2, wherein the controller is operable to determine, from an increase in current sensed by the current sensor, that a contemporaneous, sudden movement of the replaceable battery unit sensed by the motion sensor unit is indicative of a kickback event of the surgical power tool.

4. The replaceable battery unit of claim 1, wherein the motion sensor unit comprises at least one of:
   a gyroscope;
   an accelerometer; or
   a magnetometer.

5. The replaceable battery unit of claim 4, wherein the motion sensor unit comprises an inertial measurement unit (IMU).

6. The replaceable battery unit of claim 1, further comprising a brake for short circuiting windings of a motor of the surgical power tool in response to said determination of a sudden movement of the replaceable battery unit indicative of a kickback event of the surgical power tool.

7. The replaceable battery unit of claim 1, wherein the sudden movement of the replaceable battery unit comprises a rotational movement.

8. The replaceable battery unit of claim 1, wherein the one or more battery cells are rechargeable.

9. A surgical power tool including a replaceable battery unit according to claim 1.

10. The surgical power tool of claim 9, wherein the surgical power tool includes:
    a body portion; and
    a handle extending outwardly from the body portion, wherein the replaceable battery unit is attached to, or received at least partially inside, the handle.

11. The surgical power tool of claim 10, wherein the replaceable battery unit is attached to, or received at least partially inside, an end of the handle distal the body portion.

12. The surgical power tool of claim 9, wherein the surgical power tool comprises a rotational power tool.

13. A surgical kit including:
    one or more replaceable battery units according to claim 1; and
    one or more surgical power tools configured to receive said one or more replaceable battery units.

14. A surgical kit including at least one surgical power tool according to claim 1.

15. A method comprising:
operating a surgical power tool according to claim 1; and
during said operation of the surgical power tool, the controller:
- determining, from an output of the motion sensor unit, a sudden movement of the replaceable battery unit indicative of a kickback event of the surgical power tool; and
- in response to said determination, disconnecting power from the replaceable battery unit to the surgical power tool.

* * * * *